United States Patent [19]

Ogura et al.

[11] Patent Number: 5,288,702
[45] Date of Patent: Feb. 22, 1994

[54] ETHYL (1R,6S)-2,2,6-TRIMETHYLCYCLOHEX-ANECARBOXYLATE, AROMA CHEMICAL COMPOSITION CONTAINING THE SAME AND PROCESS OF PRODUCING THE SAME

[75] Inventors: Miharu Ogura; Hiroyuki Matsuda; Takeshi Yamamoto; Akemi Shimada, all of Tokyo, Japan

[73] Assignee: Takasago International Corporation, Tokyo, Japan

[21] Appl. No.: 858,187

[22] Filed: Mar. 26, 1992

[30] Foreign Application Priority Data

Mar. 26, 1991 [JP] Japan .................... 3-166543
Mar. 9, 1992 [JP] Japan .................... 4-99009

[51] Int. Cl.$^5$ .................................. A61K 7/46
[52] U.S. Cl. ............................. 512/24; 560/1
[58] Field of Search ........................ 512/24; 560/1

[56] References Cited

U.S. PATENT DOCUMENTS

| | | | |
|---|---|---|---|
| 4,411,829 | 10/1983 | Schulte-Elte et al. | 512/24 |
| 4,439,353 | 3/1984 | Schenk | 512/24 |
| 4,474,687 | 10/1984 | Schenk | 512/24 |
| 5,015,625 | 5/1991 | Fehr et al. | 512/24 |

OTHER PUBLICATIONS

Alkonyi et al, Chem. Ber., vol. 102, pp. 709–711 (1969).
Buchecker et al, Chem. Abst., vol. 80, #146366X (1974). Helv. Chim. Acta, vol. 56, pp. 2548–2563 (1973).

*Primary Examiner*—James H. Reamer
*Attorney, Agent, or Firm*—Sughrue, Mion, Zinn, Macpeak & Seas

[57] ABSTRACT

Ethyl (1R,6S)-2,2,6-trimethylcyclohexanecarboxylate represented by formula (1)

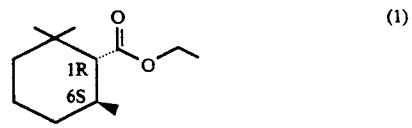

is disclosed. Also, an aroma chemical composition containing the same and a process of the production of the same are disclosed.

2 Claims, No Drawings

ETHYL (1R,6S)-2,2,6-TRIMETHYLCYCLOHEXANECARBOXYLATE, AROMA CHEMICAL COMPOSITION CONTAINING THE SAME AND PROCESS OF PRODUCING THE SAME

FIELD OF THE INVENTION

The present invention relates to an aroma chemical composition to be used for perfuming cosmetics. Also, the present invention relates to a process of producing ethyl 2,2,6-trimethylcyclohexanecarboxylate useful as an aroma chemical. Furthermore, the present invention relates to a process of producing optically active ethyl (1R,6)-2,2,6-trimethylcyclohexanecarboxylate particularly useful as an aroma chemical.

BACKGROUND OF THE INVENTION

As components of living things in the earth, there are materials showing various characteristics caused by their asymmetric structures, and it is generally known that among physiologically active materials having an asymmetric structure, those useful for a human being are frequently of specific antipodes, such tendency is particularly remarkable in the fields of, for examples, medicaments, agricultural chemicals, pheromones, and food additives, and that when they are a racemic mixture, the effect is greatly reduced, or a negative function appears. For example, JP-A-63-44544 describes that: "In the present science, while there is no single theory which can elucidate the phenomenon of the sense of smell, it has frequently been experimentally clarified that only one optically active substance of a certain compound has desired odor properties and that while a racemate thereof has similar smell character characteristics, its aroma intensity is not more than a half thereof at the most" (the term "JP-A" as used herein means an "unexamined Japanese patent application").

This is not exceptional in the field of aroma chemicals. For example, for the odor of peppermint, L-menthol is useful, for the odor of cumin, d-carvone is useful, and for the odor of grapefruit, d-nootkatone is useful, respectively, but they each has a different odor from other optical antipodes, or the odor is stronger than other optical antipodes. As recent examples, such phenomena are observed in α-ionone, hydroxycitronellal, rose oxide, etc. (see, Kagaku Sosetsu, 14 (1976), "Aji To Nioi No Kagaku (Chapter 6). Therefore, the development of optically active aroma chemicals is significant for the development of new odors or effective optical antipodes like the development of new aroma chemicals.

Ethyl 2,2,6-trimethylcyclohexanecarboxylate is a known compound already described in Chem. Ber., Vol. 102, 709-711 (1969), but its odor and value as an aroma chemical are not described therein. Also, since ethyl 2,2,6-trimethylcyclohexanecarboxylate has asymmetric carbon atoms in the molecule, while it is expected that two mirror-image isomers of a (+) isomer and a (−) isomer exist, the ethyl 2,2,6-trimethylcyclohexanecarboxylate described in the foregoing literature is a racemic mixture, and neither report regarding the individual synthesis of these isomers nor report about the properties of the isomers.

Also, as an analogue of the 2,2,6-trimethylcyclohexanecarboxylic acid ester compound known as an aroma chemical, a mixture of ethyl 2-ethyl-6,6-dimethylcyclohexanecarboxylate and ethyl 2,3,6,6-tetramethylcyclohexanecarboxylate is disclosed in JP-B-2-62542 (the term "JP-B" as used herein means an "examined published Japanese patent application"), but the properties of the individual compounds and the odor characteristics as a mixture are not shown therein.

With respect to racemic 2,2,6-trimethylcyclohexanecarboxylic acid derivatives, investigations have been made about the production process of a violet odor [see, Helv. Chem. Acta, 31, 134 (1948)]. Also, ethyl (1R,6S)-2,2,6-trimethylcyclohexanecarboxylate according to the present invention (hereinafter sometimes referred to simply as "the compound of the present invention") is a very useful aroma chemical having a fruit-like and floral odor.

The inventors carried out the process shown by the following reaction scheme for producing (1R,6S)-2,2,6-trimethylcyclohexanecarboxylic acid. That is, using optically active (3S)-7-methoxycitronellal as a raw material, enol acetate was first formed and cyclized to provide (1R,6S)-2,2,6-trimethylcyclohexanecarbaldehyde, which was then oxidized to provide (1R,6S)-2,2,6-trimethylcyclohexanecarboxylic acid, and this acid was esterified to synthesize the compound of the present invention, i.e., ethyl (1R,6S)-2,2,6-trimethylcyclohexanecarboxylate.

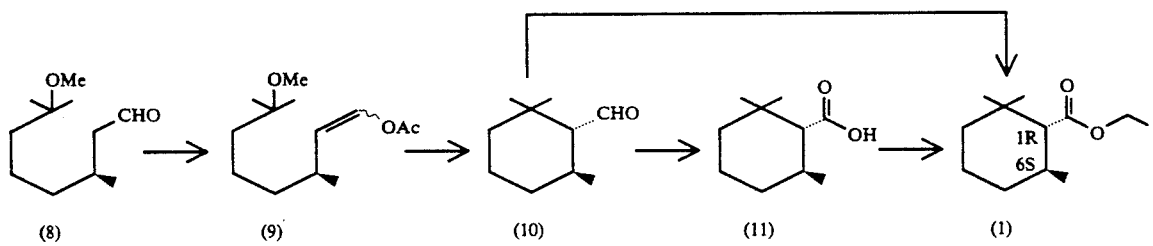

(8) (9) (10) (11) (1)

As an example of obtaining an optically active carboxylic acid by recrystallizing a carboxylic acid as a diastereomer salt of an asymmetric amine to undergo optical resolution, there are known a process of producing p-isopropyl α-methyldihydrocinnamate as described in JP-A-55-27166 and a process of producing p-tert-butyl α-methyldihydrocinnamate as described in JP-A-55-35459.

Recently, with the diversity of various fragrance cosmetics and hygienic materials, a new demand which has not been known in conventional fragrance cosmetics and hygienic materials has been being increased; the development of aroma chemical substances having strong diffusibility, specific fragrance quality, high preference, long lasting, good stability, and high safety has been required; and in particular, aroma chemical materials having a floral and fruit-like odor, which can satisfy the aforesaid requirements, are insufficient.

Accordingly, the present invention is aimed to provide an aroma chemical material or aroma chemical composition capable of satisfying the aforesaid requirements and giving a floral and fruit-like odor.

In general, it is known that in aroma chemical compositions, even a slight difference in top note, etc. of a single aroma chemical sometimes changes the fragrance quality as a product. In particular, in a high-class perfume, etc., a delicate difference of a single aroma chemical determines the propriety as the perfume. In particular, in the case of a single aroma chemical giving a floral and fruit-like odor, delicate odor factors such as naturalness and freshness are important as a value of the aroma chemical.

In regard to the relation of the steric structure and odor of the compound of the present invention, the inventors have recognized that in the geometric isomers (i.e., the cis-form and the trans-form), the trans-form is superior to the cis-form and that in the optical isomers of the trans-form [i.e., the (1R,6S)-form and the (1S,6R)-form], the (1R,6S)-form is superior to the (1S,6R)-form. In other words, the higher the ratio of the trans-form to the cis-form and the higher the optical purity, the more excellent the odor and the higher the value as an aroma chemical.

However, in the component composition of ethyl (1R,6S)-2,2,6-trimethylcyclohexanecarboxylate which was obtained first by the inventors, the content of the (1R,6S)-form as the trans-form was about 90%, and the content of the (1S,6S)-form as the cis-form was about 10%. Also, in regard to the optical purity, when not subjected to the optical resolution, while the optical purity of the product depends on the optical purity of a raw material, since commercially available (3S)-7-methoxyoitronellal as the raw material has an optical purity of 98% ee, the optical purity of the product is not higher than the foregoing optical purity. That is, there was a room for an improvement in the ethyl (1R,6S)-2,2,6-trimethylcyclohexanecarboxylate first obtained by the inventors.

Accordingly, in the component composition of ethyl (1R,6S)-2,2,6-trimethylcyclohexanecarboxylate, it was important to develop a process of producing geometrically and optically pure ethyl (1R,6S)-2,2,6-trimethylcyclohexanecarboxylate.

SUMMARY OF THE INVENTION

An object of the present invention is to develop a novel aroma chemical component giving a floral and fruit-like odor and also to provide a process of producing the foregoing novel aroma chemical component, and particularly a process of producing geometrically and optically pure ethyl (1R,6S)-2,2,6-trimethylcyclohexanecarboxylate.

Under the above-described circumstances, the inventors have made extensive investigations about the synthesis of 2,2,6-trimethylcyclohexanecarboxylic acid derivatives and odors thereof. As a result, it has been found that in regard to odor properties, ethyl 2,2,6-trimethylcyclohexanecarboxylate has strong diffusibility and a specific floral and fruit-like odor with high preference and that of the two kinds of the geometric isomers of ethyl 2,2,6-trimethylcyclohexanecarboxylate, the trans-form particularly has the foregoing odor properties.

Furthermore, as a result of syntheses of the optically active compounds of ethyl 2,2,6-trimethylcyclohexanecarboxylate, it has been discovered that of the four kinds of the optical isomers, the (1R,6S)-form particularly has the foregoing odor properties and is excellent in the odor intensity. Thus, as a result of testing the stability and safety for using as an aroma chemical material, it has been confirmed that the stability and safety of the (1R,6S)-form are very high. Moreover, as a result of perfuming testing, it has also been discovered that the (1R,6S)-form can become a useful aroma chemical. Thus, the present invention has been accomplished based on these discoveries That is, the present invention provides optically active ethyl (1R,6S)-2,2,6-trimethylcyclohexanecarboxylate represented by the following formula (1), a process of producing the same, and an aroma chemical composition containing the same.

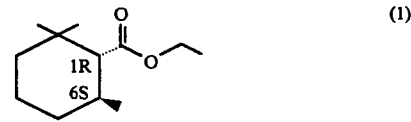

DETAILED DESCRIPTION OF THE INVENTION

Racemic ethyl 2,2,6-trimethylcyclohexanecarboxylate was investigated with respect to the fragrance quality using two kinds of synthesis processes of a synthesis process wherein the cis-form is a main component as shown in reaction scheme 1 and a synthesis process wherein the trans-form is a main component as shown in reaction scheme 2.

Reaction Scheme 1

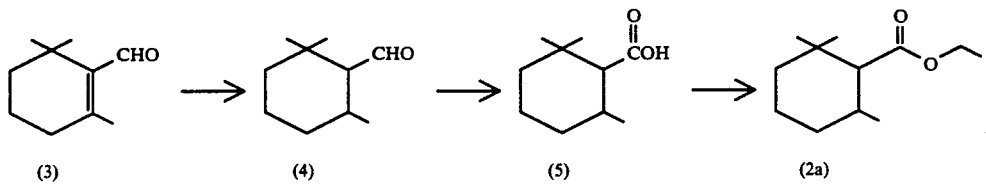

Reaction Scheme 2

-continued

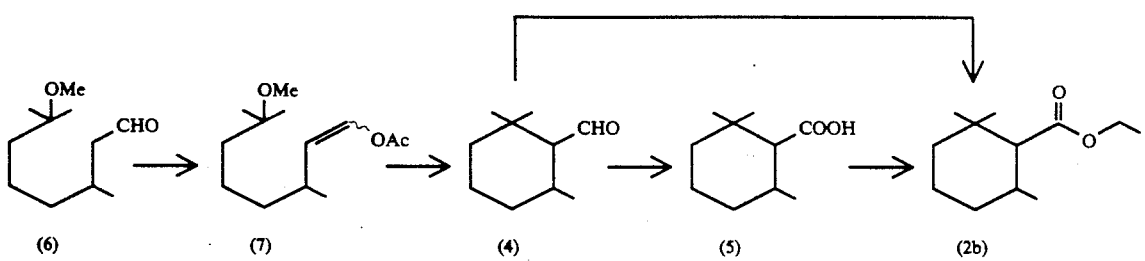

That is, in reaction scheme 1, commercially available β-cyclocitral (3) was hydrogenated using a palladium catalyst, to obtain 2,2,6-trimethylcyclohexanecarbaldehyde (4) having a composition comprising 65% of the cis-form and 35% of the trans-form, which was then oxidized with nitric acid to provide a carboxylic acid (5). This acid (5) was reacted with ethyl bromide using an equimolar amount of sodium hydroxide and a catalytic amount of a quaternary ammonium salt, to obtain ethyl 2,2,6-trimethylcyclohexanecarboxylate (2a) having a composition comprising 68% of the cis-form and 32% of the trans-form.

Also, in reaction scheme 2, commercially available 7-methoxycitronellal (6) was reacted with acetic anhydride to provide enol acetate (7), which was then subjected to a cyclization reaction using a phosphoric acid catalyst, without being purified, to obtain 2,2,6-trimethylcyclohexanecarbaldehyde (4) having a composition comprising 90% of the trans-form and 10% of the cis-form. This aldehyde (4) was oxidized and esterified in the same manner as in reaction scheme 1 described above, to obtain ethyl 2,2,6-trimethylcyclohexanecarboxylate (2b) having a composition comprising 90% of the trans-form and 10% of the cis-form.

As a result of evaluating the odor about two kinds of the samples thus obtained, it was astonishingly found that the sample containing the trans-form as a main component synthesized by the process of reaction scheme 2 has a high fragrace character intensity, a specific floral and fruit-like odor, and high preference as compared with the sample synthesized by the process of reaction scheme 1. Thus, as a result of separating the product by the process of reaction scheme 2 into the cis-form and the trans-form and confirming the odors thereof, it was clarified that the cis-form has a weak and featureless floral odor, whereas the trans-form has the foregoing desired odor features.

Then, as to the trans-form, according to the synthesis process of reaction scheme 2, ethyl (1S,6R)-2,2,6-trimethylcyclohexanecarboxylate (16) and ethyl (1R,6S)-2,2,6-trimethylcyclohexanecarboxylate (1) were respectively synthesized using commercially available optically active d-7-methoxycitronellal (12) and L-7-methoxycitronellal (8) as a raw material by the process showing in the following reaction scheme 3 and reaction scheme 4, and the fragrance quality of each product was evaluated. As a result, it was found that the odor intensity of the (1S,6R)-form (16) is about ½ of the odor intensity of the (1R,6S)-form (1) and fails in the diffusibility and feature of a specific fruit-like odor, whereas the (1R,6S)-form (1) has the foregoing excellent odor properties.

Reaction Scheme 3

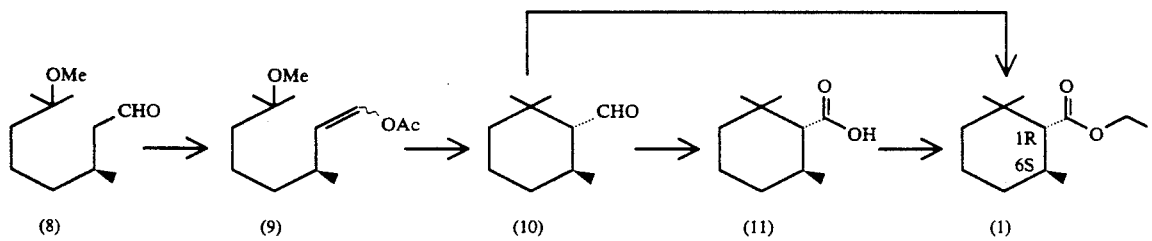

Reaction Scheme 4

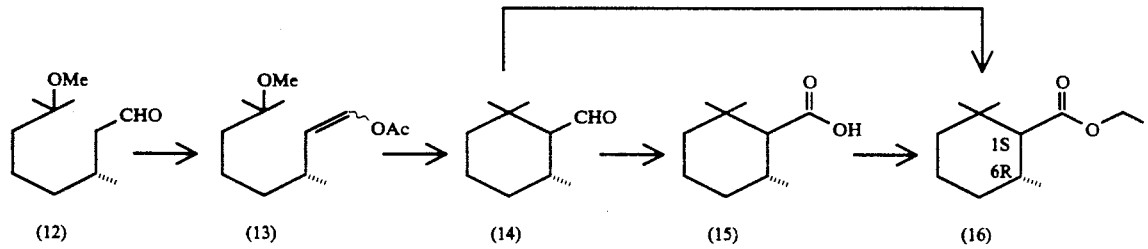

In addition, as the process of obtaining optically active 2,2,6-trimethylcyclohexanecarboxylic acid (11) or (15) using trans-2,2,6-trimethylcyclohexanecarbaldehyde (10) or (14) in reaction scheme 3 or reaction scheme 4, there are a process of using sodium chlorite as described in, for example, *Tetrahedron*, 37, 2091 (1981), a process of using ruthenium chloride and hydrogen peroxide described in, for example, *J. Org. Chem.*, 53, 3587 (1988), a process of using Caro's acid as described in, for example, *J. Org. Chem.*, 33, 2525 (1968), a process of using a heteropoly acid and hydrogen peroxide as described in, for example, *J. Org. Chem.*, 53, 3587 (1988), etc., in addition to the foregoing process of employing the nitric acid oxidation. Also, as the process of producing optically active ethyl 2,2,6-trimethylcyclohexanecarboxylate (1) or (16) by ethyl esterification of optically active 2,2,6-trimethylcyclohexanecarboxylic acid (11) or (15), usually well-known processes of reacting the carboxylic acid (11) or (15) with ethanol using an acid catalyst can be also used.

Furthermore, as the process of directly synthesizing optically active ethyl 2,2,6-trimethylcyclohexanecarboxylate (1) or (16) from optically active trans-2,2,6-trimethylcyclohexanecarbaldehyde (10) or (14), a process of reacting sodium hypochlorite and ethanol as described in, for example, *Tetrahedron, Lett.*, 23, 4647 (1982) can be used.

Also, the inventors extensively investigated a novel process of producing ethyl (1R,6S)-2,2,6-trimethylcyclohexanecarboxylate. As a result, they have succeeded in obtaining geometrically and optically pure (1R,6S) -2,2,6-trimethylcyclohexanecarboxylic acid (11) by converting racemic or optically active 2,2,6-trimethylcyclohexanecarboxylic acid into a diastereomer salt using an asymmetric amine and recrystallizing the salt. By esterification of the product, geometrically and optically pure ethyl (1R,6S)-2,2,6-trimethylcyclohexanecarboxylate (1) can be easily produced, leading to accomplishment of the present invention.

That is, the present invention also provides a process of producing geometrically and optically pure ethyl (1R,6S)-2,2,6-trimethylcyclohexanecarboxylate.

As a result of testing the safety and stability, which are necessary conditions for the use of the thus obtained optically active ethyl 2,2,6-trimethylcyclohexanecarboxylate (1) or (16) as an aroma chemical material, it was found that these compounds are almost safety in irritation and sensitivity to the human skin and, thus, have high safety. Also, it was found that these compounds show high stability in performing soaps, do not cause fading by the action of light, and are utterly stable at a pH of from 3 to 10.

Thus, a specific floral and fruit-like odor-imparting agent or an odor-improving agent having strong diffusibility and high preference containing ethyl (1R,6S)-2,2,6-trimethylcyclohexanecarboxylate (1) of the present invention can be provided, and also fragrance cosmetics, hygienic materials, medical supplies, etc., containing the compound of the present invention as an odor component can be provided. That is, the commercial values of shampoos, rinses, perfumes, colognes, hair tonics, hair creams, bases for dressing the hair, such as pomade, etc., face powders, rouges, other dressing bases and dressing detergents, soaps, dishwashing detergents, detergents for laudry, softeners, disinfecting detergents, deodorizing detergents, room aromatic agents, furniture cares, disinfectants, insecticides, bleaching agents, other various kinds of hygienic detergents, tooth pastes, mouth washers, toilet papers, perfuming agents for facilitating the administration of medial supplies, etc., can be increased by compounding therewith the compound of the present invention in a proper amount capable of imparting a unique odor.

Production Process of Raw Material Racemate

In regard to the synthesis of 2,2,6-trimethylcyclohexanecarboxylic acid mainly composed of the transform of a racemate which becomes a raw material for the optical resolution, there are, for example, two kinds of synthetic processes shown in the reaction schemes described hereinbelow.

In the 1st process, commercially available β-cyclocitral (3) is hydrogenated using a hydrogenation catalyst such as palladium, to provide 2,2,6-trimethylcyclohexanecarbaldehyde (4) mainly composed of the cisform, which is then isomerized using an acid catalyst such as phosphoric acid, to obtain 2,2,6-trimethylcyclohexanecarbaldehyde mainly composed of the trans-form (the trans-form content: 90 to 95%). Then, the aldehyde is oxidized in a usually well-known oxidation process, such as, for example, a nitric acid oxidation process, to obtain 2,2,6-trimethylcyclohexanecarboxylic acid (5) mainly composed of the trans-form.

In the 2nd process, as in foregoing reaction scheme 2, racemic 7-methoxycitronellal (6) is reacted with acetic anhydride to provide enol acetate (7), which is then cyclized with phosphoric acid, etc., to obtain 2,2,6-trimethylcyclohexanecarbaldehyde (4) mainly composed of the trans-form (the trans-form content: 88 to 93%). The aldehyde (4) is oxidized in a similar manner to obtain 2,2,6-trimethylcyclohexanecarboxylic acid (5) mainly composed of the trans-form (the trans-form content: 88 to 93%).

1st Process

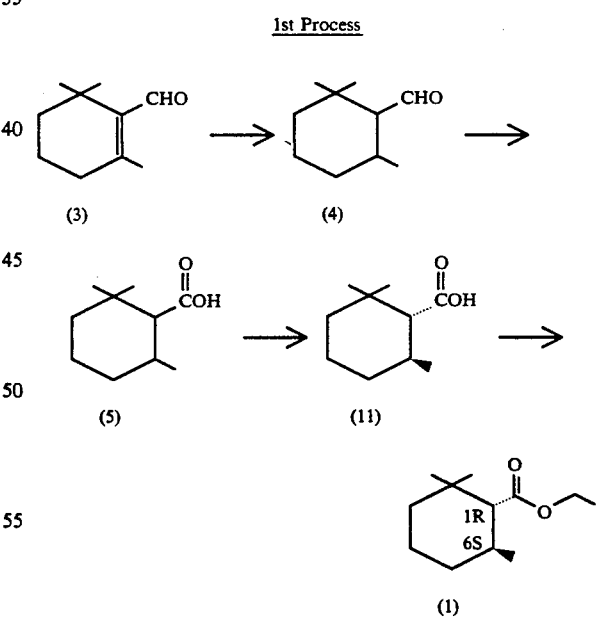

2nd Process

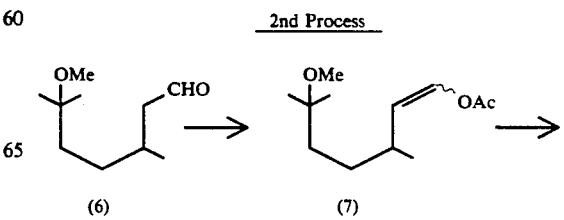

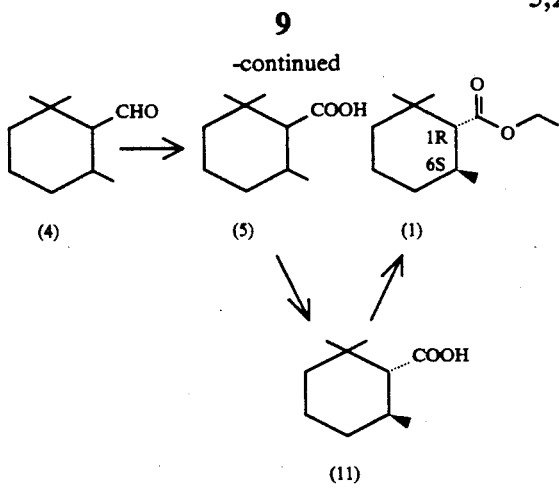

Optical Resolution of Raw Material

As an asymmetric amine which functions as a resolving agent for carrying out the optical resolution of racemic 2,2,6-trimethylcyclohexanecarboxylic acid, amines such as arylalkylamines [e.g., 1-phenylethylamine, 1-phenyl-2-tolylethylamine, and 1-(1-naphthyl)ethylamine], natural alkaloids (e.g., guinine, brucine, and cinchonine), aminoalcohols, can be used, but primary amines represented by aryl group-containing ethylamines are preferably used. Of these amines, 1-phenylethylamine and 1-(1-naphthyl)ethylamine are particularly preferable for obtaining a high optically pure product with good yield.

There is no particular restriction on a recrystallizing solvent, and any solvent which dissolves a sparingly soluble or easily soluble diastereomer salt at a temperature of from room temperature to the boiling point thereof and precipitates the diastereomer salt at room temperature as it is or by cooling, concentrating, etc., may be used. For example, alcohols such as methanol and ethanol, esters such as ethyl acetate and methyl acetate, chlorinated hydrocarbons such as chloroform and methylene chloride, ethers such as diethyl ether and diisopropyl ether, hydrocarbons such as n-hexane and benzene, and water can be used singly or as a mixture thereof. A mixed solvent system of n-hexane and ethyl acetate or a single solvent system of diisopropyl ether is particularly preferable.

The practical optical resolution is as follows.

That is, after adding 2,2,6-trimethylcyclohexanecarboxylic acid (5) and an optically active amine in the foregoing solvent singly or mixed solvent at room temperature to form the salt, the solution is heated with stirring to uniformly dissolve the salt. The temperature of the solution is slowly lowered to room temperature to selectively crystallize the dissolved diastereomer salt, and the crystals are separated, whereby the optical resolution is carried out.

In addition, at the crystallization, there is no particular need of adding seeds to the solution but for quickening the crystallization, it is effective to add a slight amount of the diastereomer salt as a seed for the crystallization.

In regard to the amount of the resolving agent used, it is preferred to use the resolving agent in the range of from about 0.7 to 1.1 equivalents to 2,2,6-trimethylcyclohexanecarboxylic acid.

The diastereomer salt thus obtained is desalted by an ordinary method, to provide desired optically active (1R,6S)-2,2,6-trimethylcyclohexanecarboxylic acid (11) shown in the foregoing reaction schemes, and at the same time, the optically active amine is recovered. For example, a diluted aqueous hydrochloric acid solution and an organic solvent are added to the diastereomer salt, followed by shaking well the mixture to decompose the salt. After separating an organic layer containing (1R,6S)-2,2,6-trimethylcyclohexanecarboxylic acid (11) from an aqueous layer containing the optically active amine hydrochloride, the organic layer is washed with water and dehydrated, and the solvent is distilled off. Then, by distillation or silica gel column chromatography, optically active (1R,6S)-2,2,6-trimethylcyclohexanecarboxylic acid (11) can be obtained. The aqueous layer is made basic with a diluted aqueous potassium hydroxide solution and after shaking well the aqueous layer together with an organic solvent and separating the organic solvent layer from the aqueous layer, the optically active amine is recovered from the organic solvent layer.

In addition, about both the optical antipodes of 2,2,6-trimethylcyclohexanecarboxylic acid, after measuring the optical rotation thereof and convering into ethyl 2,2,6-trimethylcyclohexanecarboxylate as a final product, gas chromatographic analysis by a capillary column carrying optically active cyclodextrin was carried out, and the difference in the areal percentages of both the enantiomers was used as the optical enatiometric excess (e.e.) or the optical purity (see, Hajime Nozaki, *Hoshiimonodakeo Tsukuru Kagaku*, page 236, 1983, published by Shokabo K. K.).

Also, as a process of forming geometrically and optically pure ethyl (1R,6S)-2,2,6-trimethylcyclohexanecarboxylate (1) by esterification of geometrically and optically pure (1R,6S)-2,2,6-trimethylcyclohexanecarboxylic acid (11) obtained, a process of reacting the carboxylic acid (11) and ethanol using an acid catalyst, and a process of reacting the carboxylic acid (11) in a system of sodium hydroxide (or potassium hydroxide) and ethyl bromide (or ethyl iodide) using a phase transfer catalyst are well known.

Then, the present invention is further described in more detail by the following Synthesis Examples, Test Examples, and Examples, but these Examples are for illustrating the present invention but not to limit it in any way.

SYNTHESIS EXAMPLE 1

Synthesis of ethyl 2,2,6-trimethylcyclohexanecarboxylate (2a) containing the cis-form as main component 1A): In a 500-ml autoclave, 200 g of β-cyclocitral (3) (gas chromatographic purity: 94%) and 100 g of isopropyl alcohol were reacted using 5 g of a 5% palladium-alumina catalyst at a hydrogen pressure of 5 kg/cm$^2$ and at a reaction temperature of 25° C. until a theoretical amount of hydrogen was consumed. Then, the catalyst was removed from the reaction mixture by filtration, and the isopropyl alcohol was recovered from the filtrate under reduced pressure by means of an evaporator, to provide 201 g of a concentrated oil. Then, 201 g of the concentrated oil was rectified by a 30-cm Helipack-packed still, to provide 168 g of 2,2,6-trimethylcyclohexanecarbaldehyde [boiling point: 77.5° to 79.5° C./8 mm Hg, composition by gas chromatograph (type: HEWLETT PACKARD 5890, column: Carbo wax 20M (HP) 0.2 mm×25 m, conditions: 80° C. to 220° C., 5° C./min.; hereinafter the same): trans-form content: 35%, cis-form content: 65%].

Analytical Data: MS (CI) M/e:

(4)-Trans-form: 155 (M+, 14), 139 (9), 121 (16), 111 (20), 95 (16), 84 (36), 69 (100), 55 (36), 41 (20)

(4)-Cis-form: 155 (M+, 16), 139 (8), 121 (17), 111 (21), 96 (28), 85 (69), 69 (100), 55 (42), 41 (27)

1-B): In a 300-ml 4-necked flask equipped with a condenser, a thermometer, a dropping funnel, and a stirrer was placed 39 g of nitric acid (60% aqueous solution) and heated to 55° C. To the solution was added dropwise 93 g (0.60 mole) of 2,2,6-trimethylcyclohexanecarbaldehyde (4) composed of 35% of the trans-form and 65% of the cis-form synthesized in Synthesis Example 1-A) described above over a period of 2 hours. Thereafter, the reaction was carried out for 3 hours at the same temperature. Then, 100 g of toluene and 100 g of water were added to the reaction mixture at room temperature to wash with water and form an organic layer and an aqueous layer separately. The organic layer was washed thrice with 100 g of a saturated aqueous sodium chloride solution, and the toluene was distilled off under reduced pressure by means of an evaporator, to provide 101 g of crude 2,2,6-trimethylcyclohexanecarboxylic acid (5) composed of 35% of the trans-form and 65% of the cis-form.

Analytical Data: MS (CI) M/e (5)-Trans-form: 170 (M+, 7), 152 (35), 137 (4), 127 (7), 110 (100), 100 (7), 87 (54), 69 (96), 56 (46), 41 (30), 29 (3)

(5)-Cis-form: 170 (M+, 6), 152 (35), 137 (4), 127 (7), 110 (100), 100 (55), 87 (55), 69 (91), 56 (44), 41 (30), 29 (1)

1-C): In a 300-ml 4-necked flask equipped with a condenser, a thermometer, a dropping funnel, and a stirrer were placed 55 g (0.0135 mole) of tricaprylylmethylammonium chloride (trade name: Aliquat 336) as a phase transfer catalyst and 38.0 g (0.68 mole) of potassium hydroxide, and to the mixture was added dropwise a solution composed of 46 g (0.27 mole) of 2,2,6-trimethylcyclohexanecarboxylic acid (5) synthesized in Synthesis Example 1-B) described above and 79 ml of toluene at a temperature of 40° C. or lower over a period of 30 minutes. After 20 minutes since then, 41.3 g (0.367 mole) of ethyl bromide was added dropwise to the mixture at a temperature of from 40° C. to 45° C. over a period of one hour. Furthermore, the mixture was stirred for 3 hours at the same temperature to finish the reaction. After washing the reaction mixture with water and separating an organic layer from an aqueous layer formed, the organic layer was washed with 100 ml of an aqueous 3% hydrochloric acid solution, and after further separating an organic layer from an aqueous layer, the organic layer was further washed twice with 100 ml of an aqueous soda ash solution and a saturated aqueous sodium chloride solution. Then, the organic layer formed was separated from the aqueous layer and distilled under reduced pressure by an evaporator to distill off the toluene, whereby 54 g of a concentrated oil was obtained. Then, 54 g of the concentrated oil was rectified with a Widmer still, to provide 38 g of ethyl 2,2,6-trimethylcyclohexanecarboxylate (2a) (boiling point: 98° C./10 mm Hg; gas chromatic purity: 32% of the trans-form, 68% of the cis-form).

Analytical Data: MS (CI) M/e (1)-Trans-form: 198 (M+, 8), 183 (4), 152 (87), 109 (86), 87 (53), 69 (100), 55 (62), 41 (95), 29 (96)

(1)-Cis-form: 198 (M+, 10), 183 (4), 152 (90), 129 (58), 110 (83), 87 (52), 69 (100), 55 (48), 41 (80), 29 (62)

SYNTHESIS EXAMPLE 2

Synthesis of ethyl 2,2,6-trimethoxycyclohexanecarboxylate (2b) containing the trans-form as main component 2-A): In a 2-liter 4-necked flask equipped with a condenser, a thermometer, a dropping funnel, and a stirrer were placed 305 g of acetic anhydride, 9.5 g of sodium acetate, and 247 g of triethylamine in a nitrogen gas atmosphere, the mixture was heated to 75° C. with stirring, and to the solution formed was added dropwise 350 g of commercially available racemic methoxycitranellal (6) (made by Takasago International Corporation) over a period of one hour.

Thereafter, the reaction mixture was refluxed for 6 hours at a temperature of from 101° C. to 117° C., the reaction mixture was cooled to 5° C. and washed with 200 g of water and 200 g of toluene, an organic layer was separated from an aqueous layer formed, 200 g of water was further added to the organic layer, and water washing and separation of the organic layer from the aqueous layer were carried out twice, to provide 590 g of a toluene solution of enol acetate (7). By measuring the solution with gas chromatography, it was confirmed that compound (7) has a composition composed of 29.5% of the cis-form, 62.7% of the trans-form, and 5.3% of diacetate (17).

Spectral Data: MS (CI) M/e (7)-Trans-form: 229 (M+1, 1), 197 (70), 155 (42), 137 (100), 95 (12), 73 (41)

(7)-Cis-form: 229 (M+1, 3), 197 (100), 155 (88), 137 (98), 95 (24), 73 (82)

Diacetate (17): 289 (M+1, 0.2), 197 (85), 155 (75), 137 (100), 103 (19), 73 (33)

The (7)-trans-form, the (7)-cis-form, and diacetate (17) are shown below.

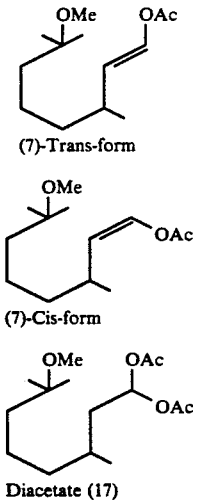

Then, in a 2 liter 4-necked flask equipped with a condenser, a thermometer, a drainage means, and a stirrer were placed 590 g of a toluene solution of compound (7) obtained in the foregoing step, 210 g of 85% phosphoric acid, and 175 g of toluene, and the mixture was refluxed (the refluxing temperature: 70° C. to 105° C.) with stirring for 3 hours in a nitrogen gas atmosphere (the refluxing temperature was controlled by removing methanol formed together with toluene from the system).

The reaction mixture was cooled to 5° C., washed with 700 ml of cold water, an organic layer formed was separated from an aqueous layer, and after washing the organic layer once with 700 ml of water, 700 ml of an aqueous 5% soda ash solution, and then 700 ml of a saturated aqueous sodium chloride solution, followed by separating the organic layer from the aqueous layer. The toluene was distilled off under reduced pressure to provide 305 g of a concentrated oil. The concentrated oil thus obtained was rectified by a 30-cm Helipack-packed still, to provide 149 g of 2,2,6-trimethylcyclohexanecarbaldehyde (4) [boiling point: 79.5° C. to 80.5° C./8 mm Hg, the composition by gas chromatography: 90% of the trans-form, 10% of the cis-form].

2-B): In a 300-ml 4-necked flask equipped with a condenser, a thermometer, a dropping funnel, and a stirrer was placed 40 g of nitric acid (60% aqueous solution) and heated to 55° C. To the solution was added dropwise 95 g (0.62 mole) of 2,2,6-trimethylcyclohexanecarbaldehyde (4) composed of 90% of the trans-form and 10% of the cis-form synthesized in Synthesis Example 2-A) described above over a period of 2 hours. Thereafter, the reaction was carried out for 3 hours at the same temperature. Then, 100 g of toluene and 100 g of water were added to the reaction mixture at room temperature to wash with water and form an organic layer and an aqueous layer separately. The organic layer was washed thrice with 100 g of a saturated aqueous sodium chloride solution, and 80 ml of the toluene was distilled off under reduced pressure by means of an evaporator, to provide 104 g of crude 2,2,6-trimethylcyclohexanecarboxylic acid (5) composed of 89% of the trans-form and 11% of the cis-form (boiling point: 44° to 54° C.). The mass spectra of the cis- and trans-forms of the acid (5) were the same as those in Synthesis Example 1.

2-C): In a 300-ml 4-necked flask equipped with a condenser, a thermometer, a dropping funnel, and a stirrer were placed 5.6 g (0.0137 mole) of tricaprylylammonium chloride (trade name: Aliquat 336) as a phase transfer catalyst and 38.9 g (0.69 mole) of potassium hydroxide, and a solution composed of 47.5 g (0.28 mole) of 2,2,6-trimethylcyclohexanecarboxylic acid (5) synthesized in Synthesis Example 2-B) described above and 80 ml of toluene was added dropwise to the mixture at a temperature of 40° C. or lower over a period of 30 minutes. After 20 minutes since then, 42.3 g (0.375 mole) of ethyl bromide was added dropwise to the mixture at a temperature of from 40° C. to 45° C. over a period of one hour. The mixture was further stirred for 3 hours at the same temperature to finish the reaction. After washing the reaction mixture with 200 ml of water and separating an organic layer from an aqueous layer formed, the organic layer was washed with 100 ml of an aqueous 3% hydrochloric acid solution, followed by separating the organic layer formed. The organic layer was washed twice with 100 ml of an aqueous 5% soda ash solution and 100 ml of a saturated aqueous sodium chloride solution, followed by separating the organic layer formed. Then, the organic layer was distilled under reduced pressure by an evaporator to distill off the toluene, whereby 55 g of a concentrated oil was obtained. Then, 55 g of the concentrated oil was rectified by a 30-cm Widmer still, to provide 39 g of ethyl 2,2,6-trimethylcyclohexanecarboxylate (2a) [boiling point: 98° C./10 mm Hg; gas chromatographic purity: 90% of the trans-form, 10% of the cis-form].

It was also confirmed that the mass spectrum of the compound (2a) was the same as that in Synthesis Example 1.

SYNTHESIS EXAMPLE 3

Synthesis of ethyl 2,2,6-trimethylcyclohexanecarboxylate (2a) directly from 2,2,6-trimethylcyclohexanecarbaldehyde (4)

In a one-liter 4-necked flask equipped with a condenser, a thermometer, a dropping funnel, and a stirrer were placed 57 g of 2,2,6-trimethylcyclohexanecarbaldehyde (4) [gas chromatographic composition: 90% of the trans-form, 10% of the cis-form] synthesized in synthesis Example 2, 45 g of acetic acid, and 250 ml of ethanol. After stirring the mixture and cooling it to 10° C., 600 g of a commercially available aqueous sodium hypochlorite solution (active chlorine content: 9.5%) was added dropwise thereto at the same temperature over a period of one hour. Thereafter, the mixture was returned to room temperature and stirred for one hour to finish the reaction. The composition of the reaction mixture by gas chromatography was comprised of 62% of ethyl 2,2,6-trimethylcyclohexanecarboxylate (2a), 27% of 2,2,6-trimethylcyclohexanecarboxylate, and 11% of other unknown components.

Then, after adding 300 g of toluene to the reaction mixture, extracting the product, and separating a toluene layer from an aqueous layer, the toluene layer was washed with an aqueous 10% sodium hydroxide solution and separated from an aqueous layer to remove the acid (5). Then, the toluene was distilled off to provide 48 g of a concentrated oil. Then, 48 g of the concentrated oil was rectified by a 15-cm Helipack-packed still, to provide 28 g of ethyl 2,2,6-trimethylcyclohexanecarboxylate (1a) [boiling point: 96.5° C. to 98° C./10 mm Hg; gas chromatographic purity: 89% of the trans-form, 11% of the cis-form].

SYNTHESIS EXAMPLE 4

Synthesis of ethyl (1R,6S)-2,2,6-trimethylcyclohexanecarboxylate (1)

4-A): In a 5-liter 4-necked flask equipped with a condenser, a thermometer, a dropping funnel, and a stirrer were placed 871 g of acetic anhydride, 27 g of sodium acetate, and 706 g of triethylamine in a nitrogen gas atmosphere, and after heating the mixture to 75° C. with stirring, 1 kg of commercially available L-methoxycitronellal (8) (made by Takasago International Corporation; $[\alpha]_D^{25} = -10.42°$, optical purity=98% ee) was added dropwise thereto over a period of one hour.

Thereafter, the reaction mixture was refluxed for 6 hours at a temperature of from 10° C. to 15° C. and cooled to 5° C., the reaction mixture was washed with 500 g of water and 500 g of toluene, and the toluene layer was separated from an aqueous layer. Then, the toluene layer was washed twice with 500 g of water, followed by separating the toluene layer from an aqueous layer in each step to provide 1690 g of a toluene solution of enol acetate (9). When the solution was analyzed by gas chromatography, the cis-form was 29.0%, the trans-form was 62.9%, and diacetate (18) was 5.5%.

The mass spectra of enol acetate and diacetate obtained in the reaction were the same as those of the (7)-trans-form, the (7)-cis-form, and diacetate (18) in Synthesis Example 2.

The trans-form [(9)-trans-form], the cis-form [(9)-cis-form], and diacetate (18) are shown below.

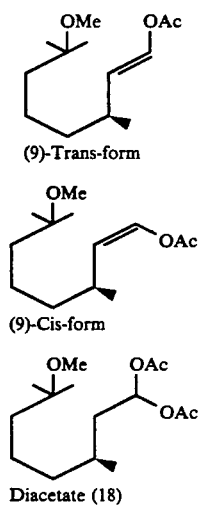

Then, in a 5-liter 4-necked flask equipped with a condenser, a thermometer, a drainage means, and a stirrer were placed 1690 g of the toluene solution of compound (9) obtained above, 620 g of 85% phosphoric acid, and 500 g of toluene, and the mixture was refluxed (refluxing temperature: 71° C. to 107° C.) with stirring for 3 hours in a nitrogen gas atmosphere (the refluxing temperature was controlled by removing slowly methanol formed together with toluene).

The reaction mixture obtained was cooled to 5° C. and washed with 2,000 ml of cold water, and an organic layer formed was separated from an aqueous layer. Furthermore, after washing once the organic layer with each of 2,000 ml of water, 2,000 ml of an aqueous 5% soda ash solution, and 2,000 ml of a saturated aqueous sodium chloride solution, followed by separating the organic layer from an aqueous layer. The toluene was distilled off under reduced pressure to provide 872 g of a concentrated oil. Then, 872 g of the concentrated oil was rectified with a 1-m Helipack-packed still to provide 425 g of optically active 2,2,6-trimethylcyclohexanecarbaldehyde (10) [boiling point: 80° C. to 81° C./8 mm Hg; $[\alpha]_D^{25} = -0.47°$; gas chromatographic purity: 90% of the trans-(1R,6S)-form, 10% of the cis-(1S,6S)-form].

The trans-(1R,6S)-form [(10)-trans-form] and the cis-(1S,6S)-form [(10)-cis-form] are shown below.

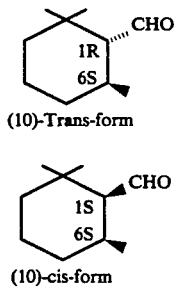

4-B): In a 300-ml 4-necked flask equipped with a condenser, a thermometer, a dropping funnel, and a stirrer was placed 42 g of nitric acid (aqueous 60% solution), and the temperature was raised to 55° C. by heating. To the solution was added dropwise 100 g (0.65 mole) of (1R,6S)-2,2,6-trimethylcyclohexanecarbaldehyde (10) [composition: 90% of the (1R,6S)-form, 10% of the (1S,6S)-form] synthesized in Synthetic Example 4-A) with stirring over a period of 2 hours. After carrying out the reaction for 3 hours at the same temperature, the reaction mixture was washed with water with 100 g of toluene and 100 g of water at room temperature, followed by separating an organic layer from an aqueous layer. The organic layer was washed thrice with 100 g of a saturated aqueous sodium chloride solution, followed by separating the organic layer from an aqueous layer. The toluene was distilled off from the organic layer by an evaporator under reduced pressure to provide 109 g of crude (1R,6S)-2,2,6-trimethylcyclohexanecarboxylic acid (11) [composition: 91% of the (1R,6S)-form, 9% of the (1S,6S)-form; melting point: 44° C. to 54° C.].

The product was recrystallized from methylene chloride as a solvent to provide 52 g of pure (1R,6S)-2,2,6-trimethylcyclohexanecarboxylic acid (11) (melting point: 67° C. to 68° C.; optical rotation $[\alpha]_D^{25} = +14.37°$).

Analytical Data of Compound (11):

$^1$H-NMR (400 MHz, CDCl$_3$) δ: 0.903 (d, 3H, J=5.94 Hz), 0.907 (m, 1H), 0.99 (s, 1H), 1.010 (s, 1H), 1.18 (m, 1H), 1.42 (m, 1H), 1.50 (m, 2H), 1.73 (m, 1H), 1.83 (m, 2H)

MS m/e: 170 (M+, 7), 152 (35), 137 (4), 127 (7), 110 (100), 100 (7), 87 (54), 69 (96), 56 (46), 41 (30), 29 (3)

IR (cm$^{-1}$): 3400–2500, 2950, 2926, 1700, 950

4-C): In a 300-ml 4-necked flask equipped with a condenser, a thermometer, a dropping funnel, and a stirrer were placed 5.9 g (0.0145 mole) of tricaprylylmethylammonium chloride (trade name: Aliquat 336) as a phase transfer catalyst and 40.9 g (0.73 mole) of potassium hydroxide, and a solution composed of 50 g (0.29 mole) of (1R,6S)-2,2,6-trimethylcyclohexanecarboxylic acid (11) synthesized in step 4-B) and 85 ml of toluene was added dropwise to the mixture at a temperature of 40° C. or lower over a period of 30 minutes. After 20 minutes since then, 44.5 g (0.395 mole) of ethyl bromide was added dropwise to the mixture at a temperature of from 40° C. to 45° C. over a period of one hour, and the mixture was further stirred for 3 hours at the same temperature to finish the reaction. The reaction mixture was washed with 200 ml of water, followed by separating an organic layer from an aqueous layer. The organic layer was washed with 100 ml of an aqueous 3% hydrochloric acid solution, followed by separating the organic layer from an aqueous layer. The organic layer was further washed twice with 100 ml of an aqueous 5% soda ash solution and 100 ml of a saturated aqueous sodium chloride solution, followed by separating the organic layer from an aqueous layer. The toluene was distilled off from the organic solvent solution obtained by an evaporator under reduced pressure to provide 58 g of a concentrated oil. Then, 58 g of the concentrated oil was rectified by a 30-cm Widmer still to provide 41 g of pure ethyl (1R,6S)-2,2,6-trimethylcyclohexanecarboxylate (1) [boiling point: 98° C./10 mm Hg; optical rotation: $[\alpha]_D^{25} = +14.14°$, gas chromatographic purity: 99.9% or higher].

Analytical Data of Ethyl (1R,6S)-Trimethylcyclohexanecarboxylate (1):

¹H-NMR (400 MHz, CDCl₃) δ: 0.826 (d, 3H, J=6.0 Hz), 0.90 (m, 1H), 0.936 (s, 3H), 0.970 (s, 3H), 1.15 (m, 1H), 1.26 (t, 3H, J=7.1 Hz), 1.39 (m, 1H), 1.50 (m, 2H), 1.69 (m, 1H), 1.79 (d, 1H, J=11.4 Hz), 1.85 (m, 1H), 4.14 (q, 2H, J=7.1 Hz)

MS m/e: 198 (M+, 8), 183 (4), 152 (27), 109 (86), 87 (53), 69 (100), 55 (62), 41 (95), 29 (96)

IR (cm⁻¹): 2925, 1740, 1460, 1385, 1240, 1195, 1040

SYNTHESIS EXAMPLE 5

Synthesis of ethyl (1S,6R)-trimethylcyclohexanecarboxylate (16)

5-A): In a 2 liter 4-necked flask equipped with a condenser, a thermometer, a dropping funnel, and a stirrer were placed 280 g of acetic anhydride, 9 g of sodium acetate, and 230 g of triethylamine in a nitrogen gas atmosphere, and while heating the mixture to 75° C. with stirring, 320 g of commercially available d-methoxycitronellal (12) (made by Takasago International Corporation, $[\alpha]_D^{25} = +10.52°$, optical purity: 98% ee) was added dropwise thereto over a period of one hour.

After refluxing (100° C. to 119° C.) the reaction mixture for 6 hours, the resulting reaction mixture was cooled to 5° C., washed with 160 g of water and 160 g of toluene, followed by separating an organic layer formed from an aqueous layer. The organic layer was further washed twice with 160 g of water, followed by separating the organic solvent solution formed from an aqueous solution to provide 540 g of a toluene solution of enol acetate (13). The gas chromatographic composition of the compound (13) was composed of 30% of the cis-form (13), 63% of the trans-form (13), and 5.0% of diacetate (19)

The mass spectra of enol acetate (13) were the same as those of the (7)-trans-form, the (7)-cis-form, and diacetate (19) in Synthesis Example 2.

The trans-form (13), the cis-form (13), and diacetate (19) formed are shown below.

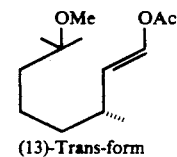

(13)-Trans-form

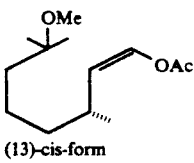

(13)-cis-form

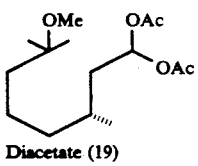

Diacetate (19)

Then, in a 2 liter 4-necked flask equipped with a condenser, a thermometer, a drainage means, and a stirrer were placed 540 g of the toluene solution of compound (13) obtained, 200 g of 85% phosphoric acid, and 160 g of toluene, and the mixture was refluxed (refluxing temperature: 80° C. to 108° C.) with stirring in a nitrogen gas atmosphere (the refluxing temperature was controlled by slowly removing methanol formed together with toluene).

The reaction mixture was cooled to 5° C. and washed with 640 ml of cold water, followed by separating an organic layer from an aqueous layer. The organic layer was washed once with 640 ml of water, 640 ml of an aqueous 5% soda ash solution, and 640 ml of a saturated aqueous sodium chloride solution, followed by separating the organic layer formed from an aqueous layer in each time to provide 280 g of a concentrated oil. The concentrated oil was rectified by a 30-cm Helipack-packed still to provide 136 g of optically active 2,2,6-trimethylcyclohexanecarbaldehyde (14) [boiling point: 79° C. to 81° C./8 mm Hg; $[\alpha]_D^{25} = +0.49°$; gas chromatographic purity: 91% of the trans-(1S,6R)-form, 9% of the cis-(1R,6R)-form].

The trans-form [(14)-trans-form] and the cis-form [(14)-cis-form] formed are shown below.

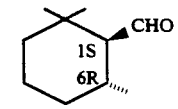

(14)-Trans-form

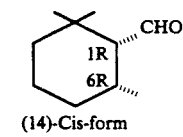

(14)-Cis-form

5-B): In a 300-ml 4-necked flask equipped with a condenser, a thermometer, a dropping funnel, and a stirrer was placed 38 g of nitric acid (aqueous 60% solution) and heated to 55° C. Then, 90 g of (1S,6R)-2,2,6-trimethylcyclohexanecarbaldehyde (14) [composition: 91% of the (1S,6R)-form, 9% of the (1R,6R)-form] synthesized in Synthesis Example 5-A) was added dropwise thereto with stirring over a period of 2 hours. After carrying out the reaction for 3 hours at the same temperature, the reaction mixture was washed with water with 90 g of toluene and 100 g of water at room temperature, followed by separating an organic layer formed from an aqueous layer. The organic layer was washed thrice with 100 g of a saturated aqueous sodium chloride solution, followed by separating the organic layer from an aqueous layer. The toluene was distilled off from an organic layer by an evaporator under reduced pressure to provide 98 g of crude (1S,6R)-2,2,6-trimethylcyclohexanecarboxylic acid (15) [composition: 91% of the (1S,6R)-form, 9% of the (1R,6R)-form]. The product was recrystallized from methylene chloride as a solvent to provide 46 g of pure (1S,6R)-2,2,6-trimethylcyclohexanecarboxylic acid (15) [melting point: 67° C. to 68° C.; optical rotation; $[\alpha]_D^{25} = -14.40°$].

5-C): In a 300-ml 4-necked flask equipped with a condenser, a thermometer, a dropping funnel, and a stirrer were placed 5.3 g (0.013 mole) of tricaprylmethylammonium chloride (trade name: Aliquat 336) as a phase transfer catalyst and 37 g (0.65 mole) of potassium hydroxide, and a solution composed of 45 g (0.26 mole) of (1S,6R)-2,2,6-trimethylcyclohexanecarboxylic acid synthesized in Synthesis Example 5-B) described above and 80 ml of toluene was added dropwise thereto at a temperature of 40° C. or lower over a period of 30 minutes. After 20 minutes since then, 40 g (0.355 mole)

of ethyl bromide was added dropwise thereto at a temperature of from 40° C. to 45° C. over a period of one hour. The mixture was further stirred for 3 hours at the same temperature to finish the reaction.

The reaction mixture obtained was washed with 200 ml of water, followed by separating an organic layer from an aqueous layer. The organic layer was washed with 100 ml of an aqueous 3% hydrochloric acid solution, followed by separating the organic layer from an aqueous layer. The organic layer was further washed twice with 100 ml of an aqueous 5% soda ash solution and 100 ml of a saturated aqueous sodium chloride solution, followed by separating the organic solvent solution. The toluene was distilled off from the organic layer by an evaporator under reduced pressure to provide 52 g of a concentrated oil. Then, 52 g of the concentrated oil was rectified with a 30-cm Widmer still to provide 37 g of pure ethyl (1S,6R)-2,2,6-trimethylcyclohexanecarboxylate (16) [boiling point: 98° C./10 mm Hg; optical rotation: $[\alpha]_D^{25} = -14.17°$; gas chromatographic purity: 99.9% or higher].

The compound (16) obtained is shown below.

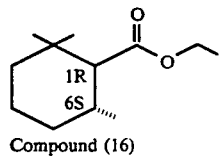

Compound (16)

TEST EXAMPLES

1) Stability Test with Soap

A soap was perfumed with ethyl 2,2,6-trimethylcyclohexanecarboxylate (2b) synthesized in Synthesis Example 2 and placed in a glass container, followed by closing tightly. The container was placed in a chamber kept at 50° C., whereby a stability test was carried out for 2 months.

As a result of determining the change of the fragrance quality by 5 expert panelists, it was found that not only any odor by the decomposed products was observed, but neither change nor deterioration of the fragrance were confirmed and, hence, the compound (2b) was stable to the passage of time. Also, for determining the stability to the sun light, when the foregoing soap was placed under the sun light for one month at room temperature to carry out the tanning test, no tanning was observed at all.

2) Stability Test with Acidic Solution

An acetic acid-acidic solution (pH 3) of ethyl 2,2,6-trimethylcyclohexanecarboxylate (2b) synthesized in Synthesis Example 2 having the following composition was prepared.

| Acetic Acid | 1 g |
| --- | --- |
| Triethyl Citrate | 50 g |
| Ethyl 2,2,6-Trimethylcyclohexane carboxylate (2b) | 10 g |
| n-Dodecane (internal standard) | 1 g |

The solution was placed in a 100-ml glass container and after storing it in a chamber kept at 40° C. for one month, the change of the composition was determined by gas chromatography. As a result, it was confirmed that no change was observed and, thus, ethyl 2,2,6-trimethylcyclohexanecarboxylate was stable under the acetic acid-acid condition.

3) Stability Test with Basic Solution

A basic solution (pH 10) of ethyl 2,2,6-trimethylcyclohexanecarboxylate (2b) synthesized in Synthesis Example 2 having the following composition was prepared.

| Triethylamine | 1 g |
| --- | --- |
| Triethyl Citrate | 50 g |
| Ethyl 2,2,6-Trimethylcyclohexane-carboxylate | 5 g |
| Water | 0.5 g |
| Methanol | 10 g |
| n-Dodecane (internal standard) | 1 g |

The solution was placed in a 100-ml glass container, and after storing the container in a chamber kept at 40° C. for one month, the change of the composition was determined by gas chromatography. As a result, it was confirmed that no change was observed and, hence, ethyl 2,2,6-trimethylcyclohexanecarboxylate (2b) was stable under the amine-basic condition (pH 10).

4) Safety Test

In regard to the safety of ethyl 2,2,6-trimethylcyclohexanecarboxylate (2b) synthesized in Synthesis Example 2, a sensitization test, a skin primary irritation test, a phytotoxicity test, and a mutation test were applied but all results were negative and hence the safety of the compound (2b) was very high.

EXAMPLE 1

An enzyme-containing bleaching agent composition having the following composition was prepared.

|  | (weight part) |
| --- | --- |
| Sodium Percarbonate | 93.7 |
| Enzyme (Alkalaze 29T, trade name, made by Novo Industry Co.) | 1.0 |
| Anhydrous Calcium Sulfate | 5.0 |
| Ethanol Solution of 50% Ethyl 2,2,6-Trimethylcyclohexanecarboxylate obtained in Synthesis Example 2 | 0.3 |
| Sum | 100.0 |

About the foregoing composition and compositions each containing ethyl 2,2,6-trimethylcyclohexanecarboxylate (2a), wherein the cis-form was the main component, obtained in Synthesis Example 1 or optically active ethyl (1R,6S)-2,2,6-trimethylcyclohexanecarboxylate (1) obtained in Synthesis Example 4 in place of the ethyl 2,2,6-trimethylcyclohexanecarboxylate (2b), wherein the trans-form was the main component, (90% of the trans-form, 10% of the cis-form) obtained in Synthesis Example 2 in the foregoing composition, comparison tests were carried out in regard to masking properties of the enzyme odor.

That is, each of the foregoing bleaching agent compositions was closed in a plastic bottle, the bottle was stored in a chamber kept at 40° C. for 30 days, and the change of the enzyme odor was determined. The evaluated results by 10 expert panelists are shown in Table 1.

TABLE 1

| Ethyl 2,2,6-Trimethyl-cyclohexanecarboxylate | (A) | (B) | (C) |
|---|---|---|---|
| Synthesis Example 4 | 10 | 0 | 0 |
| Synthesis Example 2 | 8 | 2 | 0 |
| Synthesis Example 1 | 2 | 5 | 3 |

(A) Number of panelists who did not smell the enzyme odor.
(B) Number of panelists who smelled a little the enzyme odor.
(C) Number of panelists who smelled considerably the enzyme odor.

From the results shown above, it has been found that the bleaching agent using ethyl (1R,6S)-trimethylcyclohexanecarboxylate (1) obtained in Synthesis Example 4 completely masks the enzyme odor and that the bleaching agent using ethyl 2,2,6-trimethylcyclohexanecarboxylate (2b) mainly composed of the trans-form obtained in Synthesis Example 2 also satisfies the masking effect to the enzyme odor. Also, there was no change of the fragrance quality in both of these bleaching agents.

EXAMPLE 2

Using each of ethyl 2,2,6-trimethylcyclohexanecarboxylate (2b) (90% of the trans-form, 10% of the cis-form) mainly composed of the trans-form obtained in Synthesis Example 2, ethyl 2,2,6-trimethylcyclohexanecarboxylate (2a) mainly composed of the cis-form obtained in Synthesis Example 1, and optically active ethyl (1R,6S)-2,2,6-trimethylcyclohexanecarboxylate (1) obtained in Synthesis Example 4, each of floral bouquet-like fragrances for ladies' use having the following formulations (compositions) was prepared, and the fondness was tested by 20 expert panelists.

As a result, in regard to each of formulations 1 and 2 each using ethyl (1R,6S)-trimethylcyclohexanecarboxylate (1) obtained in Synthesis Example 4 or ethyl 2,2,6-trimethylcyclohexanecarboxylate (2b) mainly composed of the trans-form obtained in Synthesis Example 2, all the panelists answered that they liked them since there was a settlement in top note as compared to the blank, and there was a tender floral smell. Also, in the case of formulation 3 using ethyl 2,2,6-trimethylhexanecarboxylate (2a) mainly composed of the cis-form obtained in Synthesis Example 1, the 5 panelists answered that formulation 3 was better than the blank, the 13 panelists answered that the effect of adding ethyl 2,2,6-trimethylcyclohexanecarboxylate was not noticed, and further the 2 panelists answered that the blank was better. In addition, in the comparison of formulation 1 with formulation 2, the 18 panelists answered that formulation 1 had a stronger diffusibility of top note and was better than formulation 2 since the formulation 1 had a fresh odor.

| | Formulation 1 | Formulation 2 | Formulation 3 | Blank |
|---|---|---|---|---|
| β-Ionone | 80 | 80 | 80 | 80 |
| Benzyl Acetate | 60 | 60 | 60 | 60 |
| Benzyl Salicylate | 120 | 120 | 120 | 120 |
| Cis-2-hexenyl salicylate | 30 | 30 | 30 | 30 |
| L-Citronellol | 34 | 34 | 34 | 34 |
| L-Hydroxyitronellal | 50 | 50 | 50 | 50 |
| Eugenol | 40 | 40 | 40 | 40 |
| Methyl Dihydrojasmonate | 20 | 20 | 20 | 20 |
| Indole | 1 | 1 | 1 | 1 |
| p-t-Butyl-α-methyldihydrocinnamine Aldehyde | 120 | 120 | 120 | 120 |
| Linalool | 80 | 80 | 80 | 80 |
| Ethylene Brassylatez | 80 | 80 | 80 | 80 |
| Rose Absolute | 30 | 30 | 30 | 30 |
| Phenylethyl Alcohol | 50 | 50 | 50 | 50 |
| Vanillin | 5 | 5 | 5 | 5 |
| Acetylcedrene | 120 | 120 | 120 | 120 |
| Compound (1)* | 10 | — | — | — |
| Compound (2b)** | 0 | 10 | 0 | 0 |
| Compound (2a)*** | — | — | 10 | — |
| Sum | 1000 | 1000 | 1000 | 990 |

*Ethyl (1R,6S)-2,2,6-trimethylcyclohexanecarboxylate (1) of Synthesis Example 4
**Ethyl 2,2,6-trimethylcyclohexanecarboxylate (2b) of Synthesis Example 2
***Ethyl 2,2,6-trimethylcyclohexanecarboxylate (2a) of Synthesis Example 1.

EXAMPLE 2

A rose base having high preference of the following formulation was prepared using ethyl 2,2,6-trimethylcyclohexanecarboxylate (2b) mainly composed of the trans-form obtained in Synthesis Example 2.

| Formulation | (weight part) |
|---|---|
| Nonyl Aldehyde | 2 |
| β-Ionone | 30 |
| Cis-3-hexenyl Acetate | 3 |
| L-Citronellol | 80 |
| L-Citronellyl Acetate | 7 |
| Garaniol | 110 |
| Phenylethyl aldehyde Dimethyl Acetal | 50 |
| Isocyclocitral | 6 |
| L-Rose Oxide | 10 |
| Cis-3-hexenol | 7 |
| Methyleugenol | 20 |
| Nerol | 20 |
| Phenylethyl Acetate | 65 |
| Phenylethyl Alcohol | 560 |
| Compound (2b)* | 30 |
| Sum | 1000 |

*Ethyl 2,2,6-trimethylcyclohexanecarboxylate (2b) of Synthesis Example 2

EXAMPLE 4

A citrus-like fragrance having high preference of the following formulation was prepared using ethyl (1R,6S)-2,2,6-trimethylcyclohexanecarboxylate (1) obtained in Synthesis Example 4.

| Formulation | (weight part) |
|---|---|
| Benzyl Acetate | 6 |
| Bergamot Oil | 100 |
| Citral | 30 |
| L-Citronellol | 10 |
| Geranyl Acetate | 60 |
| Grape Fruit Oil | 50 |
| Methyl Dihydrojasmonate | 50 |
| Heliotropin | 2 |
| Lemon Oil | 250 |
| Lime Oil | 30 |
| Linalool | 50 |
| Linalyl Acetate | 100 |
| Ethyl Brassylate | 15 |
| Orange Oil | 190 |
| Petigrain Citronia Oil | 2 |
| Phenylethyl Alcohol | 20 |
| Styrallyl Acetate | 15 |
| 4-(4-Methyl-3-pentenyl)-3-cyclohexane-1-carbaldehyde | 5 |
| Compound (1)* | 15 |
| Sum | 1000 |

*Ethyl (1R,6S)-2,2,6-trimethylcyclohexanecarboxylate (1) of Synthesis Exqample 4.

SYNTHESIS EXAMPLE 6

Synthesis of 2,2,6-trimethylcyclohexanecarboxylic acid (5) mainly composed of the racemic trans-form using cyclocitral (3) as raw material 6-A): In a 500-ml autoclave, a mixture of 200 g of β-cyclocitral (3) (gas chromatographic purity: 94%) and 100 g of isopropyl alcohol was subjected to hydrogenation reaction using 5 g of a 5% palladium-alumina catalyst at a hydrogen pressure of 5 kg/cm² and at a reaction temperature of 25° C. until a theoretical amount of hydrogen was consumed. Then, the catalyst was removed from the reaction mixture by filtration, and the isopropyl alcohol was recovered from the filtrated by an evaporator under reduced pressure to provide 201 g of a concentrated oil of crude 2,2,6-trimethylcyclohexanecarbaldehyde [the composition by gas chromatograph: 29% of the trans-form, 70% of the cis-form, and 0.3% of others].

After reacting 201 g of the concentrated oil and 20 g of p-toluenesulfonic acid using 800 ml of toluene at 80° C. for 10 hours, the reaction mixture was washed with water and neutralized by an ordinary manner to provide 197 g of a concentrated oil of crude 2,2,6-trimethylcyclohexanecarbaldehyde (4) mainly composed of the trans-form.

Then, by rectifying 197 g of the concentrated oil with a 30-cm Helipack-packed still, 138 g of 2,2,6-trimethylcyclohexanecarbaldehyde (4) [boiling point: 78.6 to 80.6° C./8 mm Hg; the composition by gas chromatography: 90.2% of the trans-form, 9.8% of the cis-form] was obtained.

The structure of the trans-form and the cis-form are as follows.

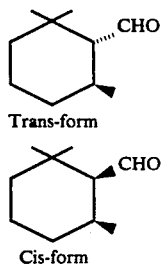

6-B): In a 300-ml 4-necked flask equipped with a condenser, a thermometer, a dropping funnel, and a stirrer was placed 39 g of nitric acid (aqueous 60% solution), and the temperature was raised to 55° C. Then, 93 g (0.60 mole) of 2,2,6-trimethylcyclohexanecarbaldehyde [composition: 90.2% of the trans-form, 9.8% of the cis-form] synthesized in Synthesis Example 6-A) was added dropwise thereto over a period of 2 hours. Thereafter, the reaction was carried out for 3 hours at the same temperature, and the reaction mixture obtained was washed with of 100 g of toluene and 100 g of water, followed by separating an organic layer from an aqueous layer. After further washing thrice the organic layer with 100 g of a saturated aqueous sodium chloride solution, the organic layer formed was separated from an aqueous layer. The toluene was distilled off from the organic layer by an evaporator under reduced pressure to provide 101 g of crude 2,2,6-trimethylcyclohexanecarboxylic acid (5) [composition: 90.5% of the trans-form, 9.5% of the cis-form].

The structures of the trans-form and the cis-form of crude 2,2,6-trimethylcyclohexanecarboxylic acid (5) obtained are shown below.

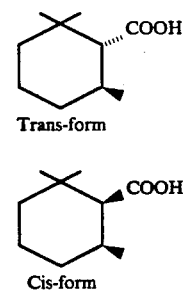

SYNTHESIS EXAMPLE 7

Optical resolution of 2,2,6-trimethylcyclohexanecarboxylic acid using optically active α-naphthylethylamine To 10.800 ml of n-hexane was added 90.0 g (0.528 mole) of 2,2,6-trimethylcyclohexanecarboxylic acid mainly composed of the racemate obtained in Synthesis Example 6 [90.5% of the trans-form, 9.5% of the cis-form] was added at room temperature, and 90.3 g of (R)-(+)-1-(1-naphthyl)ethylamine was further added thereto with stirring to form precipitates. To the reaction system containing the precipitates was added 810 ml of ethyl acetate, and the mixture was heated with stirring to dissolve the precipitates to form a homogenous solution. After stopping the heating, the solution was allowed to stand overnight as it was. The crystals thus formed were similarly recrystallized 4 times (5 times in the sum total) to provide 20.4 g of a white acicular crystal of a (1R,6S)-trimethylcyclohexanecarboxylic acid-(R)-(+)-1-(1-naphthyl)ethylamine salt [melting point: 102° C. to 105° C., $[\alpha]_D^{24} = +27.6°$ (c=0.51, EtOH)]. The percent yield for the product was 11.3%.

Then, the salt obtained was stirred in a mixture of 300 ml of 10% hydrochloric acid and 900 ml of diethyl ether for 30 minutes at room temperature, followed by separating a diethyl ether layer formed from an aqueous layer. The diethyl ether layer was washed with 300 ml of a saturated aqueous sodium chloride solution, and after dehydrating over anhydrous sodium sulfate, the solvent was distilled off to provide 10.2 g of optically active (1R,6S)-2,2,6-trimethylcyclohexanecarboxylic acid (11) [melting point: 68° C. to 69° C., $[\alpha]_D^{24} = +14.3°$ (c=1.01, EtOH), gas chromatographic purity: 99.9% of the trans-form, 0.1% of the cis-form]. In addition, the aqueous layer was made basic (ph 10) with 48.8 g of sodium hydroxide and then extracted with 700 ml of diethyl ether, whereby 9.3 g of (R)-(+)-1-(1-naphthyl)ethylamine was recovered.

The optical purity of the recovered (1R,6S)-2,2,6-trimethylcyclohexanecarboxylic acid was determined as follows. That is, after converting the carboxylic acid into the optically active desired compound, i.e., ethyl (1R,6S)-2,2,6-trimethylcyclohexanecarboxylate by an ethylation method using toluene as a solvent as well as potassium hydroxide and ethyl bromide in the presence of a phase transfer catalyst, the analysis was carried out by an optically active capillary column (50 ml×0.25 mm) carrying CP-cyclodextrin-B-236-M-19 under a constant condition at 85° C., and from the difference of the areal percentage of two kinds of diastereomers obtained, the optical purity was determined to be 97.5% ee.

SYNTHESIS EXAMPLE 8

Optical resolution of 2,2,6-trimethylcyclohexanecarboxylic acid using optically active α-phenylethylamine To 1,080 ml of diisopropyl ether was added 27.0 g (0.159 mole) of optically active 2,2,6-trimethylcyclohexanecarboxylic acid ($[\alpha]_D^{25} = +14.37°$) having an optical purity of 98% ee obtained in Synthesis Example 4-B) at room temperature, and 19.2 g (0.159 mole) of (+)-1-phenylethylamine [hereinafter referred to as "(+)-PEA"] was further added thereto with stirring to form precipitates. The reaction system containing the precipitates was heated with stirring to dissolve the precipitates and form a homogenous solution, and the heating was stopped. The solution was allowed to stand overnight as it was. Crystals thus formed were recrystallized again (total twice) similarly, to provide 15.2 g of a white acicular crystal of a (+)-PEA salt [melting point: 71° C. to 73° C., $[\alpha]_D^{24} = +21.0°$ (c=0.99, EtOH)]. The percent yield for the product was 56.3%.

The salt obtained was stirred in a mixture of 200 ml of 10% hydrochloric acid and 600 ml of diethyl ether for 30 minutes at room temperature. After separating a diethyl ether layer formed from an aqueous layer, the diethyl ether layer was washed with 200 ml of a saturated aqueous sodium chloride solution, followed by separating the diethyl ether layer formed from an aqueous layer. After dehydrating the diethyl ether layer over anhydrous sodium sulfate, the solvent was distilled off to provide 8.8 g of (1R,6S)-2,2,6-trimethylcyclohexanecarboxylic acid (11) [melting point: 70° C.; $[\alpha]^{24} = +14.7°$ (c=0.51, EtOH); gas chromatographic purity: 100%].

The structure of (1R,6S)-2,2,6-trimethylcyclohexanecarboxylic acid (11) [compound (11)] obtained is as follows.

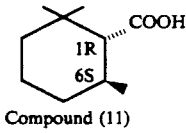

Compound (11)

In addition, after making the aqueous layer basic (pH 10) with 32.5 g of sodium hydroxide, the aqueous layer was extracted with 500 ml of diethyl ether to recover 5.7 g of (+)-PEA.

The optical purity of the (1R,6S)-2,2,6-trimethylcyclohexanecarboxylic acid (11) was determined to be 99.99% ee by the method described in Synthesis Example 7.

In addition, the esterification of the foregoing optically resolved (1R,6S)-2,2,6-trimethylcyclohexanecarboxylic acid (11) was carried out by the following manner.

In a 100-ml 4-necked flask-equipped with a condenser, a thermometer, a dropping funnel, and a stirrer were placed 10.2 g (0.0025 mole) of tricaprylylmethyl ammonium chloride (trade name: Aliquat 336) as a phase transfer catalyst and 7.0 g (0.126 mole) of potassium hydroxide, and a solution composed of 8.5 g (0.05 mole) of (1R,6S)-2,2,6-trimethylcyclohexanecarboxylic acid (11) and 15 ml of toluene was added dropwise thereto at a temperature of 40° C. or lower over a period of 30 minutes. After 20 minutes since then, 7.6 g (0.068 mole) of ethyl bromide was added dropwise to the mixture at a temperature of from 40° C. to 45° C. over a period of one hour. The mixture was further stirred for 3 hours at the same temperature to finish the reaction.

The reaction mixture obtained was washed with 37 ml of water, followed by separating an organic layer formed from an aqueous layer. The organic layer was washed with 19 ml of an aqueous 3% hydrochloric acid solution, followed by separating the organic layer from an aqueous layer. The organic layer was further washed twice with 19 ml of an aqueous 5% soda ash solution and 19 ml of a saturated aqueous sodium chloride solution, followed by separating the organic layer. The toluene was distilled off from the organic layer by an evaporator under reduced pressure to provide 10.0 g of a concentrated oil. Then, 10.0 g of the concentrated oil was rectified with a micro still to provide 6 g of ethyl (1R,6S)-2,2,6-trimethylcyclohexanecarboxylate (1) (boiling point: 99° C./10 mm Hg).

The gas chromatographic purity of the product analyzed by gas chromatography was 100%, and the optical purity thereof analyzed by an optically active analysis column was 99.99% ee. [[$\alpha]_D^{24} = +13.0°$ (c=1.06, ethanol; $n_D^{22} = 1.446$]

The product was used for the sample in the following example.

EXAMPLE 5

Using each of ethyl (1R,6S)-2,2,6-trimethylcyclohexanecarboxylate (1) having an optical purity of 100% obtained in Synthesis Example 7 and ethyl (1R,6S)-2,2,6-trimethylcyclohexanecarboxylate (1) having an optical purity of 98% ee obtained in Synthesis Example 4-C), each of floral bouquet-like fragrances for ladies' use having following formulations was prepared and the fondness was tested by 20 expert panelists.

As a result, the 15 panelists answered that formulation 1 using the product obtained in Synthesis Example 7 was better since in this case, there was a settlement in top note, the fragrance was more fresh, and had a natural tender floral odor. Also, the 4 panelists answered that both the odors were almost the same as each other, and the one panelist answered that formulation 2 using the product obtained in Synthesis Example 4-C) was better.

|  | Formulation 1 | Formulation 2 |
| --- | --- | --- |
| β-Ionone | 80 | 80 |
| Benzyl Acetate | 60 | 60 |
| Benzyl Salicylate | 120 | 120 |
| Cis-3-hexenyl Salicylate | 30 | 30 |
| L-Citronellol | 34 | 34 |
| L-Hydroxycitronellal | 50 | 50 |
| Eugenol | 40 | 40 |
| Methyl Dihydrojasmonate | 20 | 20 |
| Indol | 1 | 1 |
| p-t-Butyl-α-methyldihydrocinnamic Aldehyde | 120 | 120 |
| Linalool | 80 | 80 |
| Ethylene Brassylate | 80 | 80 |
| Rose Absolute | 30 | 30 |
| Phenylethyl Alcohol | 50 | 50 |
| Vanillin | 5 | 5 |
| Acetyl cedrene | 120 | 120 |
| Compound (1)* | 10 | — |
| Compound (1)** | — | 10 |

|  | Formulation 1 | Formulation 2 |
|---|---|---|
| Sum | 1000 | 1000 |

*Ethyl (1R,6S)-2,2,6-trimethylcyclohexanecarboxylate (1) (optical purity 99.99% ee) synthesized in Synthesis Example 7
**Ethyl (1R,6S)-2,2,6-trimethylcyclohexanecarboxylate (1) (optical purity 98% ee) synthesized in Synthesis Example 4-C).

The present invention provides an aroma chemical composition containing industrially useful ethyl 2,2,6-trimethylcyclohexanecarboxylate, in particular, the optically active form thereof. That is, ethyl (1R,6S)-2,2,6-trimethylcyclohexanecarboxylate obtained by the present invention is excellent in properties as an aroma chemical, and the aroma chemical composition containing the optically active form is used in wide fields such as various fragrance cosmetics, hygienic materials, medical supplies, coating compositions, etc.

While the invention has been described in detail and with reference to specific embodiments thereof, it will be apparent to one skilled in the art that various changes and modifications can be made therein without departing from the spirit and scope thereof.

What is claimed is:

1. Ethyl (1R,6S)-2,2,6-trimethylcyclohexanecarboxylate represented by formula (1):

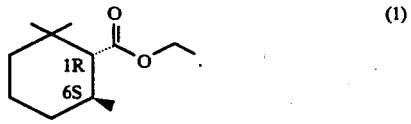

(1)

2. An aroma chemical composition containing ethyl (1R,6S)-2,2,6-trimethylcyclohexanecarboxylate represented by formula (1):

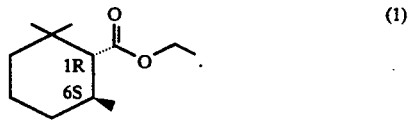

(1)

* * * * *